United States Patent

Hirose et al.

[11] Patent Number: 5,849,888
[45] Date of Patent: Dec. 15, 1998

[54] AZOAMIDE COMPOUND

[75] Inventors: Seiji Hirose; Kazuo Shiraki, both of Saitama, Japan

[73] Assignee: Wako Pure Chemical Industries, Ltd., Osaka, Japan

[21] Appl. No.: 806,633

[22] Filed: Feb. 26, 1997

[30] Foreign Application Priority Data

Mar. 1, 1996 [JP] Japan .................................. 8-071167

[51] Int. Cl.$^6$ .................................. C07C 245/04
[52] U.S. Cl. ..................... 534/886; 526/219; 526/346
[58] Field of Search ............................................. 534/886

[56] References Cited

U.S. PATENT DOCUMENTS 2,877,102  3/1959  Levesque ............................ 534/886 X
3,309,297  3/1967  Takayama et al. ................. 534/886 X
5,001,228  3/1991  Shiraki et al. ...................... 534/886 X

FOREIGN PATENT DOCUMENTS 356 026 A  2/1990  European Pat. Off. .

OTHER PUBLICATIONS

English Abstract of JP 1247401 A. Oct. 3, 1989.
European Search Report for EP 97 10 3064 dated Jun. 13, 1997.
Makromol, Chem. 193, pp. 2843–2860, "On the Kinetics of Polymerization and Copolymerization of Poly(oxyethylene) Macromonomers and Styrene", Jan. 13, 1992, by CAPEK et al.

*Primary Examiner*—Fiona T. Powers
*Attorney, Agent, or Firm*—Armstrong, Westerman, Hattori, McLeland & Naughton

[57] ABSTRACT

Azoamide compounds shown by the general formula [1]

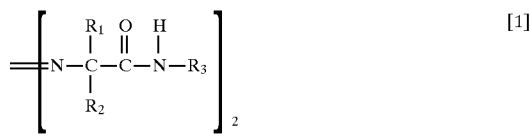

(Wherein $R^1$ and $R^2$ are independently a lower alkyl group, and $R^3$ is a saturated alkyl group having 2 or more carbon atoms) and their use.

6 Claims, No Drawings

AZOAMIDE COMPOUND

BACKGROUND OF THE INVENTION

The present invention relates to an azo compound useful as a polymerization initiator, etc., which is oily soluble and active at high temperature.

Azo compounds and organic peroxides have been known as organic radical polymerization initiator.

Organic peroxides are generally instable against impact and heating, and subjected to self-induced decomposition, which gives fear of burning and explosion.

On the other hand, azo compounds are relatively stable from physico-chemical point of view though their high activity and thus they have such an advantage as being easy in controlling a polymerization reaction. As azo compounds have recently been expanded in their use, there have been desired azo type polymerization initiators having various degrees of activities in accordance with their purposes. Particularly, there have been desired azo type polymerization initiators having activity at high temperature for the purposes of treating remaining monomer upon polymerization of styrene and of conducting cross-linking polymerization.

As azo type polymerization initiators having activity at high temperature, there have been known, for example, 1,1-azobis (1-cyanocyclohexane), 2,2'-azobis (2,4,4-trimethylpentane), etc. However, 1,1-azobis (1-cyanocyclohexane) has a cyano group in the molecule, and thus there is a possibility of generating toxicity by this cyano group, and 2,2'-azobis (2,4,4-trimethylpentane) has such a defect that it has a melting point around room temperature and thus is inconvenient in handling, etc.

Further, among amide type azo compounds, there are generally many compounds having activity at high temperature, but all of known azoamide compounds such as 2,2'-azobis (2-methylpropionamide), 2,2'-azobis (2-methyl-N-methyl-propionamide) and 2,2'-azobis [2-methyl-N-(hydroxymethyl)-propionamide] [Japanese Patent Publication-Kokoku-No.78288/1994; Makromol. Chem., 193 2843 (1992); Japanese Patent Publication-Kokai-No.149551/1990, etc.], etc., are water-soluble, which causes such defect that they are poor soluble in an organic solvent used as a solvent in conducting solution polymerization of an oily soluble monomer and thus these azoamide compounds were hard to use for the solution polymerization. For this reason, azoamide compounds having activity at high temperature and being oily soluble have been desired.

In order to improve this defect, 2,2'-azobis (2-methyl-N-allyl-propionamide), wherein an allyl group is introduced in an amino group, has been reported (Japanese Patent Publication-Kokai-No. 149551/1990, etc.).

However, though the compound is improved in its activity at high temperature, the allyl group is subjected to chain-transfer reaction to terminate the polymerization reaction, and thus a large amount of this compound is necessary to use. Improvement to this defect has also been desired.

The present invention has been completed under the circumstances as mentioned above, and the object of the present invention is to provide a novel azoamide compound having activity at high temperature, high solubility in organic solvents and high melting point.

SUMMARY OF THE INVENTION

The present invention is concerned with an azoamide compound shown by the general formula [1]

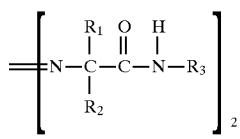

(wherein $R_1$ and $R_2$ are independently a lower alkyl group, and $R_3$ is a saturated alkyl group having 2 or more carbon atoms).

The present invention is also concerned with a method for polymerization of a monomer, which comprises subjecting the monomer to a polymerization reaction, using the above-mentioned azoamide compound as a polymerization initiator.

The present invention is further concerned with a polymerization initiator comprising the above-mentioned azoamide compound.

DESCRIPTION OF THE PREFERRED EMBODIMENT

The azoamide compound shown by the above general formula [1] of the present invention is obtained, for example, by reacting an azodicarboxylic acid diester of the following general formula [2]

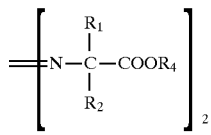

(wherein $R_1$, and $R_2$ are the same with the above and $R_4$ is a lower alkyl group.) with an amine compound shown by the following general formula [3]

$$R_3—NH_2 \qquad [3]$$

(wherein $R_3$ is the same with the above.) in the absence or presence of a solvent, and in the presence of an alkaline organic metal compound.

The lower alkyl group shown by $R_1$ and $R_2$ in the general formulas [1] and [2] may be any of straight chained, branched or cyclic ones, and includes, for example, those having 1 to 6 carbon atoms, which are specifically exemplified by methyl, ethyl, n-propyl, isopropyl, n-butyl, isobutyl, sec-butyl, tert-butyl, pentyl, isopentyl, tert-pentyl, 1-methylpentyl, n-hexyl, isohexyl, cyclopropyl, cyclopentyl and cyclohexyl, etc. The saturated alkyl group having 2 or more carbon atoms shown by $R^3$ in the general formula [1] and [3] may be any of straight chained, branched or cyclic ones, which are specifically exemplified by ethyl, n-propyl, isopropyl, n-butyl, isobutyl, sec-butyl, pentyl, isopentyl, tert-pentyl, 1-methylpentyl, n-hexyl, isohexyl, heptyl, octyl, nonyl, decyl, undecyl, dodecyl, hexadecyl, octadecyl, cyclopropyl, cyclopentyl and cyclohexyl, etc., among which one having 2 to 10 carbon atoms, preferably one having 2 to 6 carbon atoms, more preferably one having 3 to 6 carbon atoms can be mentioned. The lower alkyl group shown by $R^4$ in the general formula [2] may be any of straight chained or branched ones, and includes, for example, those having 1 to 6 carbon atoms, which are specifically exemplified by methyl, ethyl, n-propyl, isopropyl, n-butyl, isobutyl, tert-butyl, sec-butyl, pentyl, isopentyl, tert-pentyl, 1-methylpentyl, n-hexyl and isohexyl, etc.

The alkaline organic metal compound used in the production of the azoamide compound of the present invention includes, for example, an alkaline metal alkoxide such as sodium methoxide, sodium ethoxide, potassium methoxide, potassium ethoxide and potassium tert-butoxide, and organic lithium compound such as n-butyl lithium and tert-butyl lithium.

The reaction solvent includes, for example, a hydrocarbon such as toluene, xylene, benzene, cyclohexane, n-hexane and n-octane, an alcohol such as methanol, ethanol, n-propanol, isopropanol, n-butanol, isobutanol and tert-butanol, dimethyl formamide, dimethyl sulfoxide, etc. They may be used alone or in combination of two or more thereof An amount of the azodicarboxylic acid diester compound and that of the amine compound to be used in the production of the azoamide compound of the present invention are different depending upon the kind of the amine compound, and generally the amine compound is used in a range of 1.5 to 10, preferably 2 to 5 times as much moles as that of the azodicarboxylic acid diester compound.

An amount of the alkaline organic metal compound to be used is different depending upon the kind of the amine compound, and generally 0.05 to 3, preferably 0.1 to 0.5 equivalent to the azodicarboxylic acid diester compound.

A reaction temperature is not limited in particular, but when it is too high, the azo group is decomposed, and when it is too low, reaction rate is decreased to require a long reaction time, and thus it is selected from a range of 0° to 40° C.

A reaction time is different depending upon the kinds of the azodicarboxylic acid diester compound and the amine compound, and it is generally selected from a range of 1 to 24 hours As the azodicarboxylic acid diester compound and the amine compound of the present invention, commercially available ones can be used, or they may be prepared in house.

In the azoamide compound of the present invention, its azo group can easily be decomposed by heating or irradiation with light to generate radicals as well as nitrogen gas, and therefore it can be used effectively as a polymerization initiator and a blowing agent. When a monomer exists in the system upon decomposition, the monomer is rapidly polymerized.

Polymerization or copolymerization of a monomer with the use of the azoamide compound of the present invention as a polymerization initiator can be conducted, for example, as follows.

That is, the azoamide compound obtained by the above method and a monomer are subjected to polymerization reaction after a conventional manner in the absence or presence of a solvent under inert gas atmosphere, if necessary.

Treatment, etc., after the reaction can be conducted by a manner which has been usually used in this kind of field.

The monomer includes, but not limited to, for example, an α-olefin type aromatic hydrocarbon of 8 to 20 carbon atoms such as styrene, 4-methylstyrene, 4-ethlstyrene, divinylbenzene, etc., a vinylester of 3 to 20 carbon atoms such as vinyl formate, vinyl acetate, vinyl propionate and isopropenyl acetate, a halogenated vinyl compound of 2 to 20 carbon atoms such as vinyl chloride, vinylidene chloride, vinylidene fluoride, tetrafluoroethylene and tetra chloroethylene, an α,β-ethylenically unsaturated caboxylic acid of 3 to 20 carbon atoms such as acrylic acid, methacrylic acid, itaconic acid, maleic acid, fumaric acid, crotonic acid, citraconic acid, mesaconic acid, vinylacetic acid, allylacetic acid and vinylbenzoic acid, and those acids may form their salts such as alkali metal (e.g. Li, Na, K) and ammonium salts, an α, β-ethylenically unsaturated carboxylic acid ester of 4 to 20 carbon atoms such as methyl methacrylate, ethyl methacrylate, propyl methacrylate, butyl metacrylate, 2-ethylhexyl methacrylate, stearyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate, methyl citraconate, ethyl citraconate, methyl mesaconate, ethyl mesaconate and methyl 3-butenoate, a vinyl compound having cyano group of 3 to 20 carbon atoms such as acrylonitrile, methacrylonitrile and allyl cyanide, a vinyl type amide compound of 3 to 20 carbon atoms such as acrylamide and methacrylamide, an α,β-ethylenically unsaturated carboxylic acid aldehyde of 3 to 20 carbon atoms such as acrolein and crotonaldehide, a vinylsulfonic acid of 2 to 20 carbon atoms such as vinylsulfonic acid and 4-vinylbenzenesulfonate, a vinyl type aliphatic amine of 2 to 20 carbon atoms such as vinylamine and allylamine, a vinyl type aromatic amine of 8 to 20 carbon atoms such as vinylaniline, a vinyl type aliphatic heterocyclic amine of 5 to 20 carbon atoms such as N-vinyl-pyrrolidone and vinylpiperidine, a vinyl type aromatic heterocyclic amine of 5 to 20 carbon atoms such as vinylpyridine and vinylimidazol, an α, β-ethylenically unsaturated carboxylic acid alcohol of 3 to 20 carbon atoms such as allyl alcohol and crotyl alcohol, an olefin type phenol of 8 to 20 carbon atoms such as 4-vinylphenol, a diene type compound of 4 to 20 carbon atoms such as butadiene and isoprene.

These monomers may be used alone or in combination of two or more thereof

The molecular weight may be controlled, if desired, by using a chain transfer agent such as lauryl mercaptan, octyl mercaptan, butyl mercaptan, 2-mercaptoethanol and butyl thioglycolate upon conducting the polymerization reaction.

The method of the polymerization reaction mentioned above may be any of polymerization reaction such as, for example, solution polymerization, bulk polymerization, suspension polymerization and emulsion polymerization. Upon the polymerization, conventional radical polymerization initiator (e.g. azobisisobutyronitrile, dimethyl 2,2'-azobisisobutyrate, etc.) may be co-used with the azoamide compound of the present invention.

A solvent to be used in a solution polymerization method includes, for example, an ether such as tetrahydrofuran, diethylether and dioxane, a halogenated hydrocarbon such as chloroform, methylene chloride and 1,2-dichloroethane, a hydrocarbon such as n-hexane, petroleum ether, toluene, benzene and xylene, an alcohol such as methanol, ethanol and isopropanol, a ketone such as acetone, methyl ethyl ketone and methyl isobutyl ketone, acetonitrile, N,N-dimethylformamide, dimethyl sulfoxide, etc. These solvents may be used alone or in combination of two or more thereof The polymerization reaction is desirably conducted under inert gas atmosphere. The inert gas includes nitrogen gas, argon gas, etc.

A ratio of azoamide compound of the present invention to the polymerizable monomer to be used in the above polymerization reaction is different depending upon the kind of the compound of the present invention and is generally selected from a wide range of usually 0.01 to 100 wt %, preferably 0.05 to 50 wt% relative to the polymerizable monomer.

A concentration of the polymerizable monomer in the polymerization reaction is different depending upon the kind of the polymerizable monomer and is selected from a range of generally 5 to 100 wt%, preferably 10 to 60 wt%.

A polymerization temperature is not specifically limited, but when it is too low, degree of decomposition of the azo group is small and thus polymerization reaction proceeds slowly and when it is too high, too much azo groups are decomposed and thus the polymerization reaction is difficult to control. Therefore, it is generally selected from a range of 20° to 150° C., preferably 50° to 130° C. As the azoamide compound of the present invention shows activity at high temperature, it can advantageously be used in a polymerization reaction at high temperature, for example, 90°~150° C., practically 90°~120° C.

A polymerization reaction time is different depending upon reaction conditions such as a reaction temperature, the kinds of the azoamide compound and the polymerizable monomer or concentration thereof, and generally selected from a range of 2 to 24 hours.

The present invention is further explained in details in the following with citation of examples, but the present invention is not limited to those examples.

EXAMPLES

EXAMPLE 1

Synthesis of 2,2'-azobis (N-cyclohexyl-2-methyl propionamide)

47.3 Grams of cyclohexylamine is mixed with 50 g of dimethyl 2,2'-azobis (2-methylpropionate) and 20 g of 28% sodium methoxide solution in methanol is dropwise added thereto under stirring, following by conducting a reaction at room temperature with stirring for 6 hours and keeping standing overnight. 100 Milliliter of water is added to the reaction solution and cooled to 10° C. to precipitate crystals. The crystals are recovered by filtration and dried to give 59.4 g (yield 81 %) of 2,2'-azobis (N-cyclohexyl-2-methylpropionamide) as yellow crystals. The solubility is shown in Table 1.

m.p. 116° C.

IR (KBr) vcm$^{-1}$ : 3344(NH), 1645 (C=O).

$^{1}$H—NMR δppm (CDCl$_3$): 1.2 to 2.0 (m, 20H, cyclohexyl), 1.33 (s, 12H, =N—C(C$\underline{H}_3$)$_2$), 3.87 (m, 2H, cyclohexyl(NH—C$\underline{H}$)), 6.7 (br, 2H, CON$\underline{H}$).

EXAMPLE 2

Synthesis of 2,2'-azobis [N-(2-methylpropyl)-2-methyl propionamide ]

34.9 Grams of isobutylamine is mixed with 50 g of 2,2'-azobis (2-methyl propionate), and 10 g of 28% sodium methoxide solution in methanol is dropwise added thereto with stirring, followed by conducting a reaction at room temperature with stirring for 6 hours and keeping standing overnight. 100 Milliliter of water is added to the reaction solution and cooled to 10° C. to precipitate crystals. The crystals are recovered by filtration and dried to give 56.4 g (yield 83%) of 2,2'-azobis [N-(2 -methylpropyl)-2-methyl propionamide] as pale yellow crystal. The solubility is shown in Table 1.

m.p. 100° C.

$^{1}$H—NMR δppm (CDCl$_3$): 0.92 (m, 12H, CH(C$\underline{H}_3$)$_2$), 1.35 (s, 12H, =N—C(C$\underline{H}_3$)$_2$), 1.82 (m, 2H, C$\underline{H}$(CH$_3$)$_2$), 3.2 (m, 4H, NH—C$\underline{H}_2$), 6.9(br, 2H, CON$\underline{H}$).

EXAMPLE 3

Synthesis of 2,2'-azobis (N-butyl-2-methyl propionamide)

34.9 Grams of n-butylamine is mixed with 50 g of 2,2'-azobis (2-methyl propionate), and 10 g of 28% sodium methoxide solution in methanol is dropwise added thereto with stirring, followed by conducting a reaction at room temperature with stirring for 6 hours and keeping standing overnight. 100 Milliliter of water is added to the reaction solution and cooled to 10° C. to precipitate crystals. The crystals are recovered by filtration and dried to give 58.0 g (yield 85.5%) of 2,2'-azobis [N-butyl-2-methyl propionamide] as pale yellow crystal. The solubility is shown in Table 1.

m.p. 65° C.

IR (KBr) vcm$^{-1}$ : 3331 (NH), 1660 (C=O).

$^{1}$H—NMR δppm (CDCl$_3$): 0.94 (t, 6H, CH$_2$C$\underline{H}_3$), 1.3 to 1.6 (m, 8H, CH$_2$C$\underline{H}_2$), 1.34 (s, 12H, =N—C(CH$_3$)$_2$), 3.5 (m, 4H, NH—C$\underline{H}_2$), 6.85 (br, 2H, CON$\underline{H}$).

EXAMPLE 4

Synthesis of 2,2'-azobis [N-(2-methylethyl)-2-methyl propionamide ]

28.2 Grams of isopropylamine is mixed with 50 g of 2,2'-azobis (2-methyl propionate), and 20 g of 28% sodium methoxide solution in methanol is dropwise added thereto with stirring followed by conducting a reaction at room temperature with stirring for 6 hours and keeping standing overnight. 100 Milliliter of water is added to the reaction solution and cooled to 10° C. to precipitate crystals. The crystals are recovered by filtration and dried to give 41.5 g (yield 67%) of 2,2'-azobis [N-(2 -methylethyl)-2-methyl propionamide] as pale yellow crystal. The solubility is shown in Table 1.

m.p. 103° C.

IR (KBr) vcm$^{-1}$ : 3388 (NH), 1664 (C=O).

$^{1}$H—NMR δppm (CDCl$_3$): 1.8 (d, 12H, CH(C$\underline{H}_3$)$_2$), 1.33 (s, 12H, =N—C(C$\underline{H}_3$)$_2$), 4.15 (m, 2H, NH—C$\underline{H}$(CH$_3$)$_2$,), 6.85 (br, 2H, CON$\underline{H}$).

EXAMPLE 5

Synthesis of 2,2'-azobis (N-hexyl-2-methyl propionamide)

28.2 Grams of n-hexylamine is mixed with 50 g of 2,2'-azobis (2-methyl propionate), and 20 g of 28% sodium methoxide solution in methanol and 10 ml of methanol are added thereto with stirring followed by conducting a reaction at room temperature with stirring for 6 hours and keeping standing overnight. 100 Milliliter of water is added to the reaction solution and extraction with 100 ml of n-hexane is conducted. The hexane layer is washed with water and dried over anhydrous sodium sulfate. The solvent is removed by distillation to give 76.3 g (yield 95%) of 2,2'-azobis (N-hexyl-2-methyl propionamide) as pale yellow sintering crystal. The solubility is shown in Table 1.

IR (KBr) vcm$^{-1}$ : 3340 (NH), 1647 (C=O).

$^{1}$H—NMR δppm (CDCl$_3$): 0.88 (m, 6H, CH$_2$C$\underline{H}_3$), 1.3 (m, 12H, NH—CH2CH$_2$C$\underline{H}_2$C$\underline{H}_2$C$\underline{H}$2CH$_3$), 1.34 (s, 12H, =N—C(C$\underline{H}_3$)$_2$), 1.55 (m, 4H, NH —CH2C$\underline{H}_2$CH$_2$CH$_2$CH$_2$CH$_3$,),3.35 (m, 4H, NH—C$\underline{H}_2$CH$_2$CH$_2$CH$_2$CH$_2$CH$_3$.), 6.85 (br, 2H, CON$\underline{H}$).

EXAMPLE 6

Synthesis of 2,2'-azobis (N-propyl-2-methyl propionamide)

28.3 Grams of propylamine is mixed with 50 g of 2,2'-azobis (2-methyl propionate), and 10 g of 28% sodium methoxide solution in methanol and 10 ml of methanol are added thereto with stirring, followed by conducting a reaction at room temperature with stirring for 6 hours and keeping standing overnight. 100 Milliliter of water is added to the reaction solution and cooled to 5° C. to precipitate crystals. The crystals are recovered by filtration and dried to give 54.0 g (yield: 87%) of 2,2'-azobis(N-propyl-2-methyl propionamide) as pale yellow crystal. The solubility is shown in Table 1.

m.p. 65° C.

IR (KBr) vcm$^{-1}$ : 3335 (NH), 1653 (C=O).

$^1$H—NMR δppm (CDCl$_3$): 0.94 (t, 6H, NH—CH$_2$CH$_2$C$\underline{H}_3$), 1.34 (s, 12H, =N—C(C$\underline{H}_3$)$_2$), 1.57 (m, 4H, NH—CH$_2$C$\underline{H}_2$H$_3$), 3.32 (q, 4H, NH—C$\underline{H}_2$—CH$_2$—CH$_3$), 6.85 (br, 2H, CON$\underline{H}$).

EXAMPLE 7

Synthesis of 2,2'-azobis (N-ethyl-2-methyl propionamide)

50 Grams of 2,2'-azobis (2-methyl propionate) is mixed with 50 ml of methanol, and 39 g of ethylamine hydrochloride is added thereto with stirring, and 133 g of 28% sodium methoxide solution in methanol is dropwise added thereto at 5° C., followed by conducting a reaction at room temperature with stirring for 6 hours and keeping standing overnight. 200 Milliliter of water is added to the reaction solution and cooled to 5° C. to precipitate crystals. The crystals are recovered by filtration and dried to give 16.6g (yield: 30%) of 2,2'-azobis (N-ethyl-2-methyl propionamide) as pale yellow crystal. The solubility is shown in Table 1.

m.p. 98° C.

IR (KBr) vcm$^{-1}$ : 3394 (NH), 1667 (C=O).

$^1$H-NMR δppm (CDCl$_3$): 1.18 (t, 6H, NH—CH$_2$—C$\underline{H}_3$), 1.34 (s, 12H, =N—C(C$\underline{H}_3$)$_2$), 3.39 (m, 4H, NH—C$\underline{H}_2$CH$_3$), 6.8 (br, 2H, CON$\underline{H}$).

Comparative Example 1. Synthesis of 2,2'-azobis (N-methyl-2-methyl propionamide)

50 Grams of 2,2'-azobis (2-methyl propionate) is mixed with 37.1 g of 40% methylamine solution in methanol, and 10g of 28% sodium methoxide in methanol is added thereto with stirring, followed by conducting a reaction at room temperature with stirring for 7 hours and keeping standing overnight. The reaction solution cooled to 5° C. to precipitate crystals. The crystals are recovered by filtration and dried to give 37.2g (yield : 75%) of 2,2'-azobis (N-methyl-2-methyl propionamide) as pale yellow crystal. The solubility is shown in Table 1.

m.p. 153° C.

IR (KBr) vcm$^{-1}$ : 3393 (NH), 1665 (C=O).

$^1$H—NMR δppm (CDCl$_3$): 1.35 (s, 12H, =N—C(C$\underline{H}_3$)$_2$), 2.92 (s, 6H, NH—C$\underline{H}_3$), 6.9 (br, 2H, CON$\underline{H}$).

TABLE 1

| Example | Solubility (g)*) | |
| --- | --- | --- |
| | ethyl acetate | toluene |
| Example 1 | 3.5 | 5.5 |
| Example 2 | 14.0 | 8.0 |
| Example 3 | easily soluble | easily soluble |
| Example 4 | 11.0 | 5.0 |
| Example 5 | easily soluble | easily soluble |
| Example 6 | easily soluble | easily soluble |
| Example 7 | 11.0 | 4.0 |
| Comparative example | 1.2 | 0.5 ↓ |

*)Solubility of each azoamide compound in 100 g of the solvent at 25° C.

A polymerization initiator having solubility of generally 2% or more, preferably 5% or more has high applicability, and it can be found from the above Table 1 that any of the azoamide compounds of the present invention is suitable for a polymerization reaction using an organic solvent.

On the other hand, 2,2'-azobis (N-methyl-2-methyl propionamide) obtained by comparative example 1 has low solubility to ethyl acetate and toluene. Therefore, it is found that 2,2'-azobis (N-methyl-2-methyl propionamide) has low utility to polymerization reaction using such solvent.

Experiment 1. Half-life test

1 Percent (w/w) solution of each azoamide compound obtained in Examples 1 to 7 in ethyl benzene is prepared. A concentration of the azoamide compound is measured in a thermostat at pre-determined interval by 1 hour unit and a coefficient of decomposition rate constant at each temperature is obtained and then the temperature for 10-hour half life is calculated on the basis of the coefficient by Arrhenius equation. The result is shown in Table 2.

TABLE 2

| Example | temperature (°C.) for 10-hour half life |
| --- | --- |
| Example 1 | 111.0 |
| Example 2 | 112.0 |
| Example 3 | 110.6 |
| Example 4 | 111.2 |
| Example 5 | 111.6 |
| Example 6 | 110.8 |
| Example 7 | 109.6 |

From the above results, it is found that the all of the temperatures for 10-hour half life are around 110° C. and that any of the azoamide compounds of the present invention have activity at high temperature.

Experiment 2

5 ml of styrene containing a 4×10$^{-4}$M of azoamide compound which is obtained example 1, 3, or 6 were placed in individual glass tubes. After deairing, the tubes were sealed under reduced pressure. Each tube was placed into the thermostat adjusted at 110° C. to carry out the polymerization. The tube was took out from the thermostat after predetermined time, cooled under ice water immediately to stop polymerization. The reaction solution was poured into methanol to deposit and precipitate the obtained polymer. The precipitate was recovered by filtration, and dried at 60° C. under reduced pressure for 8 hours. The weight of the polymer obtained was measured and the conversion was calculated. The result is shown in Table 3.

TABLE 3

| azoamide compound | polymerization time(h) | | | | | | decomposition rate constant (sec$^{-1}$ at 110° C.) |
| --- | --- | --- | --- | --- | --- | --- | --- |
| | 1 | 2 | 3 | 4 | 6 | 8 | |
| | Conversion(%) | | | | | | |
| Example 1. | 8.7 | 20.5 | 30.8 | 41.2 | 62.5 | 81.0 | 1.72 × 10$^{-5}$ |
| Example 3. | 9.2 | 20.8 | 30.8 | 41.0 | 61.2 | 82.9 | 1.79 × 10$^{-5}$ |
| Example 6. | 9.0 | 20.0 | 31.2 | 41.0 | 62.4 | 83.6 | 1.74 × 10$^{-5}$ |

From the above results, the azoamide compounds of the present invention shows high polymerization activity in the polymerization of styrene.

As explained above, the present invention shows excellent effect in providing novel azoamide compounds having activity at high temperature, high solubility in organic solvents, high melting point and high polymerization activity.

What is claimed is:

1. An azoamide compound shown by the general formula [1]

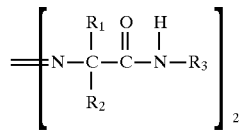

[1]

(wherein $R_1$ and $R_2$ are independently a lower alkyl group, and $R_3$ is a saturated alkyl group having 2 or more carbon atoms).

2. An azoamide compound according to claim 1, wherein the $R_3$ is a saturated alkyl group having 2 to 10 carbon atoms.

3. An azoamide compound according to claim 1, wherein the $R_3$ is a saturated alkyl group having 2 to 6 carbon atoms.

4. An azoamide compound according to claim 1, wherein the $R_3$ is a saturated alkyl group having 3 to 6 carbon atoms.

5. An azoamide compound according to claim 1, wherein the $R_1$ and $R_2$ are methyl group respectively.

6. A polymerization initiator, which comprises an azoamide compound as claimed in claim 1.

* * * * *